United States Patent
Bodelin et al.

(12) 
(10) Patent No.: US 6,264,933 B1
(45) Date of Patent: Jul. 24, 2001

(54) COMPOSITION FOR COATING KERATIN FIBRES

(75) Inventors: Sophie Bodelin, Vanves; Daniéle Debert, Savigny sur Orge, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/467,774

(22) Filed: Dec. 20, 1999

(30) Foreign Application Priority Data

Dec. 21, 1998 (FR) .................................. 98 16131

(51) Int. Cl.⁷ .............................. A61K 7/032; A61K 7/00
(52) U.S. Cl. ............................................ 424/70.7; 424/401
(58) Field of Search ...................... 424/70.7, 63

(56) References Cited

U.S. PATENT DOCUMENTS

| | | | |
|---|---|---|---|
| 3,734,874 | 5/1973 | Kibler et al. | 260/29.2 |
| 3,937,811 | 2/1976 | Papantoniou et al. | 424/64 |
| 4,233,196 | 11/1980 | Sublett | 260/29.2 |
| 4,304,901 | 12/1981 | O'Neill et al. | 528/290 |
| 5,595,198 * | 1/1997 | Kemmerer | 132/218 |
| 5,876,704 * | 3/1999 | Collin et al. | 424/63 |

FOREIGN PATENT DOCUMENTS

| | | |
|---|---|---|
| 0 611 170 | 8/1994 | (EP) . |
| 0 832 637 | 4/1998 | (EP) . |
| 2 232 303 | 3/1975 | (FR) . |
| 2 758 084 | 7/1998 | (FR) . |
| 2 238 242 | 5/1991 | (GB) . |
| WO 91/12793 | 9/1991 | (WO) . |
| WO 96/03964 | 2/1996 | (WO) . |

OTHER PUBLICATIONS

English language abstract of EP 0 611 170.
English language Derwent Abstract of FR 2 758 084.

* cited by examiner

Primary Examiner—Shelley A. Dodson
Assistant Examiner—Konata M. George
(74) Attorney, Agent, or Firm—Finnegan, Henderson, Farabow, Garrett & Dunner, L.L.P.

(57) ABSTRACT

A cosmetic composition for coating keratin fibers, in particular the eyelashes. The composition can provide a waterproof coating that curls the keratin fibers. The composition comprises at least one lamellar filler, and an aqueous phase dispersed in a liquid fatty phase containing at least one volatile organic solvent. The aqueous phase contains a polymer system comprising at least one film-forming polymer which is dispersed in the aqueous phase in the form of solid particles.

43 Claims, No Drawings

COMPOSITION FOR COATING KERATIN FIBRES

The present invention relates to a composition for coating keratin fibres, in particular human eyelashes and hair, comprising a film-forming polymer and a filler. The invention also relates to the use of this composition for making keratin fibres curl, as well as to a process for coating these keratin fibres. The composition and the coating process according to the invention are more particularly intended for substantially longilinear keratin fibres, such as the eyelashes, the eyebrows and the hair, including false eyelashes and hair pieces. The composition may be a make-up composition, a make-up base, a composition to be applied over a make-up, also known as a top-coat, or a composition for cosmetically treating keratin fibres. The invention more particularly relates to a mascara.

In general, compositions for coating the eyelashes, known as mascaras, comprise waxes for covering the eyelashes. These waxes can be dispersed in an aqueous medium, in particular with the aid of surfactants. However, the film of make-up obtained with these compositions has a tendency to crumble over time. The film thus embrittled has a tendency to no longer be resistant to rubbing, in particular with the fingers, and/or to water, for example when bathing or taking a shower, which runs counter to the production of a make-up effect which has good staying power over time.

So-called "waterproof" mascaras are also known, which comprise waxes in an anhydrous medium, in particular in a liquid fatty phase comprising organic solvents. These compositions can also comprise an aqueous phase dispersed in a liquid fatty phase, as is described, for example, in International publication WO-A-91/12793. This document moreover points out that waterproofing of the mascara can be improved by adding a water-soluble film-forming polymer to the aqueous phase. However, these compositions do not make it possible to obtain good curling of the eyelashes.

The aim of the present invention is to provide a composition for coating keratin fibres, in particular the eyelashes, which leads, after it has been applied, to a waterproof coating that imparts good curling to keratin fibres.

The inventors have found, surprisingly, that such a coating of keratin fibres, in particular of the eyelashes, can be obtained using a film-forming polymer and a lamellar filler in a composition comprising an aqueous phase dispersed in a liquid fatty phase. This gives a composition which, after it has been applied to the keratin fibres, leads to a waterproof coating which imparts good curling to keratin fibres. Moreover, the curling obtained is better than that obtained with spherical fillers, such as rice starch.

Furthermore, the coating obtained with the inventive composition does not crumble and has good resistance to rubbing, in particular to rubbing with the fingers. The coating also imparts an elongation effect to the eyelashes.

More specifically, a subject of the present invention is a cosmetic composition for coating keratin fibres, in particular the eyelashes, comprising an aqueous phase dispersed in a liquid fatty phase that contains at least one volatile organic solvent, the aqueous phase containing a polymer system comprising at least one film-forming polymer, characterized in that the film-forming polymer is in the form of solid particles dispersed in the aqueous phase, and in that the composition also comprises at least one lamellar filler.

Another subject of the invention is a mascara product comprising a reservoir containing a mascara composition as defined above and fitted with a system for applying the composition to keratin fibres, in particular the eyelashes.

A subject of the invention is also a process for coating keratin fibres, in particular the eyelashes, which comprises applying a composition as defined above to keratin fibres.

A subject of the invention is also the use of a polymer system comprising at least one film-forming polymer and at least one lamellar filler, in a composition for coating keratin fibres, in particular the eyelashes, for curling keratin fibres and/or for providing waterproofing and/or for lengthening keratin fibres, the composition comprising an aqueous phase dispersed in a liquid fatty phase that contains at least one volatile organic solvent, the film-forming polymer being in the form of solid particles dispersed in the aqueous phase.

In the present patent application, the expression "composition for coating keratin fibres" means a composition which is capable of forming a film on keratin fibres.

The expression "film-forming polymer" means a polymer which by itself leads to an isolatable film.

The expression "polymer in the form of solid particles dispersed in the aqueous phase," which is generally known as a latex or pseudolatex, means an aqueous phase in which the polymer in particulate form is directly dispersed.

The film-forming polymer in the polymer system in the form of solid particles dispersed in the aqueous phase can be chosen from polycondensates, radical-generated polymers and polymers of natural origin.

Preferably, the polymer system is capable of forming a film which produces, at a concentration of 7% in water, a shrinkage of isolated stratum corneum of more than 1% at 30° C., and at a relative humidity of 40%, preferably more than 1.5%, and better still more than 2%, gives good curling of the keratin fibres. This retraction is measured using an extensiometer according to the measuring method indicated in the examples set forth herein below.

Polycondensates which may be mentioned are anionic, cationic, nonionic or amophoteric polyurethanes, polyurethane-acrylics, polyurethane-polyvinylpyrrolidones, polyester-polyurethanes, polyether-polyurethanes, polyurea-urethanes, polyureas, polyesters (which are described in particular in U.S. Pat. Nos. 3,734,874, 4,233, 196 and 4,304,901), and mixtures thereof.

Appropriate film-forming polymers which are preferably used are polyester-polyurethanes, and more particularly polyester-polyurethanes capable of forming a film which has a hardness ranging from 40 to 200 seconds, and better still, from 50 to 170 seconds. It is possible, for example, to use the polyester-polyurethanes sold under the names "Avalure UR-425", "Avalure UR-430", "Avalure UR-405" and "Avalure UR-410," by the company Goodrich.

It is also possible to use polyether-polyurethanes, and more particularly polyether-polyurethanes capable of forming a film with a hardness ranging from 10 to 40 seconds, and better still, from 20 to 35 seconds. Examples of polyether-polyurethanes which may be mentioned are those sold under the names "Sancure 878," "Avalure UR-450" and "Sancure 861," by the company Goodrich.

The hardness of the polymer film is measured on a film obtained after drying a 300 μm thick layer of an aqueous 28% dispersion of solids of the particles of film-forming polymer for a period of 24 hours at 30° C. and at 50% relative humidity. The hardness of the film is measured according to ASTM standard D-43-66, or standard NF-T 30-016 (October 1981), using a Persoz pendulum.

Suitable film-forming polymers according to the invention which can also be used are anionic polyesters and in particular those comprising at least one monomer bearing a group —$SO_3M$, in which M represents a hydrogen atom, an ammonium ion $NH_4^+$ or a metal ion. The copolyester can be, for example, a copolymer of at least one dicarboxylic acid, of at least one diol and of at least one difunctional aromatic monomer bearing a group —SO$_3$M, in which M represents a hydrogen atom, an ammonium ion NH$_4^+$ or a metal ion.

The dicarboxylic acid can be chosen from phthalic acid, isophthalic acid and terephthalic acid. The diol can be chosen from ethylene glycol, diethylene glycol, triethylene glycol, 1,3-propanediol, 1,4-cyclohexanedimethanol and 1,4-butanediol. The difunctional aromatic monomer bearing the group —SO$_3$M can be chosen from sulphoisophthalic acid, in particular the sodium salt of 5-sulphoisophthalic acid, sulphoterephthalic acid, sulphophthalic acid and 4-sulphonaphthalene-2,7-dicarboxylic acid.

Preferred polyesters which can be used include a polyester containing repeating units of isophthalic acid, of diol and of sulphoisophthalic acid, and in particular the sulphopolyesters obtained by condensation of diethylene glycol, cyclohexanedimethanol, isophthalic acid and sulphoisophthalic acid. Sulphopolyesters which can be used are those sold under the name AQ55S, by the company Eastman.

Radical-generated polymers which may be mentioned are acrylic polymers, acrylic/styrene copolymers, and vinyl copolymers, such as vinyl ester copolymers.

When the film-forming polymer does not make it possible by itself to obtain a film which has the characteristics mentioned above, it is possible to add a compound whose function is to modify the properties of the film-forming polymer in order to obtain the desired polymer system. Thus, according to one embodiment of the composition according to the invention, the polymer system can comprise at least one film-forming auxiliary agent for obtaining a film which has the characteristics described above. The auxiliary film-forming agent makes it possible, in particular, to obtain a film which imparts good curling to the eyelashes.

The auxiliary film-forming agent can be chosen from any compound known to those skilled in the art as being capable of fulfilling the desired function, and can be chosen in particular from plasticizers and coalescence agents. This auxiliary agent can be water-soluble or water-insoluble and can optionally be in the form of an aqueous dispersion. The film-forming auxiliary agent may be added to the polymer system so that the polymer system comprises a mixture of one or more film-forming polymers and at least one auxiliary film-forming agent.

In particular, mention may be made, alone or as a mixture, of the usual plasticizers or coalescence agents, such as:

glycols and derivatives thereof, such as diethylene glycol ethyl ether, diethylene glycol methyl ether, diethylene glycol butyl ether, diethylene glycol hexyl ether, ethylene glycol ethyl ether, ethylene glycol butyl ether, ethylene glycol hexyl ether;

glycerol esters;

propylene glycol derivatives, and in particular propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether, diethylene glycol methyl ether, and propylene glycol butyl ether;

esters of acids, in particular carboxylic acids, such as citrates, phthalates, adipates, carbonates, tartrates, phosphates and sebacates;

oxyethylenated derivatives, such as oxyethylenated oils, in particular plant oils such as castor oil; and silicone oils.

The amount of auxiliary film-forming agent can be chosen by a person skilled in the art on the basis of his or her general knowledge, so as to obtain a polymer system that leads to a film having the desired mechanical properties, while at the same time retaining cosmetically acceptable properties in the composition.

The composition can comprise from 0.05% to 10% by weight, preferably from 0.1 to 7%, of film-forming polymer solids in the form of particles dispersed in the aqueous medium, relative to the total weight of the composition.

The polymer system used (polymer(s) or polymer and plasticizer) according to the invention may be present in particular in an active material (A.M.) amount ranging from 0.05 to 15%, and better still from 0.1 to 10% of the total weight of the composition.

The size of the film-forming polymer particles can range from 10 nm to 500 nm, and preferably from 20 nm to 300 nm.

The aqueous phase of the composition can consist essentially of water. It can also comprise a mixture of water and water-miscible solvent, such as lower monoalcohols containing from 1 to 5 carbon atoms, $C_3$–$C_4$ ketones, or $C_3$–$C_4$ aldehydes. A water-miscible solvent which can preferably be used is ethanol. The content of water-miscible solvent can range from 0.1% to 15% by weight, and better still, from 1 to 8% by weight, relative to the total weight of the composition.

The total weight of the aqueous phase in the composition according to the invention can range from 1% to 35% by weight relative to the total weight of the composition, and preferably from 1% to 20% by weight.

The aqueous phase of the composition can also comprise an additional water-soluble film-forming polymer which is present, in particular, in a content ranging from 0.01% to 5% by weight relative to the total weight of the composition.

Water-soluble polymers which can be mentioned in particular are:

water-soluble cellulose-based polymers, such as hydroxyethylcellulose, hydroxypropylcellulose, carboxymethylcellulose, hydroxypropylethylcellulose and ethylhydroxyethylcellulose;

keratin derivatives such, as keratin hydrolysates and sulphonic keratins;

anionic, cationic, amphoteric and nonionic chitin or chitosan derivatives, and in particular hydroxypropylchitosan;

cellulose derivatives, such as hydroxyethylcellulose, hydroxypropycellulose, methylcellulose, ethylhydroxyethylcellulose and carboxymethylcellulose, as well as quaternized cellulose derivatives;

acrylic polymers and copolymers, such as polyacrylates or polymethacrylates;

polyvinyl alcohols and polyvinylpyrrolidones;

vinyl copolymers, such as copolymers of methyl vinyl ether and of malic anhydride, or the copolymer of vinyl acetate and of crotonic acid;

polyethylene glyclols; and polymers of natural origin, which may be modified, such as:

gum arabics, guar gum, xanthan derivatives and karaya gum;

alginates and carrageenates;

glycoaminoglycans, hyaluronic acid and its derivatives;

shellac resin, sandarac gum, dammar resins, elemis gums and copal resins; and deoxyribonucleic acid.

The lamellar filler present in the composition is preferably a lamellar mineral filler. This lamellar filler makes it possible to obtain, with the film-forming polymer, good curling of keratin fibres, in particular the eyelashes.

The lamellar filler used according to the invention can be present in the form of particles with an average size of less than 40 μm, and in particular ranging from 0.5 μm to 30 μm.

Lamellar fillers which can be used in particular are:

talc, which is a hydrated magnesium silicate, and in particular those sold under the names "Talc Luzenac 00" by the company Luzenac, "Talc P3" by the company Nippon Talc;

kaolin, which is a hydrated aluminium silicate present in the form of particles of anisotropic form which are generally less than 30 μm in size; a kaolin which can be used is the one sold under the name "Kaolin Supreme 1" from English China Clays;

boron nitride, and in particular those sold under the names "Ceram Blanche 1" and "Ceram Blanche" by the company SPCI;

mica, or aluminosilicate, which can be chosen from muscovite, phlogopite, tiotite, sericite, lepidolite, paragonite, margarite, roscoelite, artificial or synthetic mica which has a fluorine atom substituting the hydroxyl group of natural mica, as well as the fired or calcined products these micas. The micas are generally in the form of flakes with sizes ranging from 2 to 200 μm, preferably 5 to 70 μm, and a thickness ranging from 0.1 to 5 μm, preferably from 0.2 to 3 μm; micas which can be used, for example, are those sold under the names "Mica SFG70" the company Aspanger and "Mica Concord 1000," by the company Sciama;

lamellar silica, in particular such as the products sold under the names "SG Flake 3 M" by the company Maprecos and "Chemicelen" by the company Sumitomo;

and mixtures thereof.

Talc is preferably used as lamellar filler.

The lamellar filler can be present in the composition according to the invention in a content ranging from 0.5% to 10% by weight relative to the total weight of the composition, and better still, from 0.5% to 5% by weight.

The liquid fatty phase of the composition comprises at least one volatile organic solvent.

In the present invention, the expression "liquid fatty phase" means any non-aqueous medium which is liquid at room temperature and immiscible with water.

The expression "volatile organic solvent" means an organic solvent which is capable of evaporating at room temperature from a support onto which it has been applied, in other words a solvent which has a measurable vapor pressure at room temperature.

It is possible in particular to use one or more oils which are volatile at room temperature and atmospheric pressure and which have, for example, a vapor pressure, at room temperature and pressure, of >0 mmHg (0 Pa) and in particular ranging from $10^{-3}$ to 300 mmHg (0.13 Pa to 40,000 Pa), on condition that the boiling point is above 30° C. These volatile oils facilitate, in particular, application of the composition to the skin, mucous membranes and superficial keratinous body growths, including for example, hair, and eyelashes. These oils can be hydrocarbon-based oils or silicone-based oils.

According to one embodiment of the invention, the volatile organic solvent can be a volatile hydrocarbon-based oil. The expression "hydrocarbon-based oil" means an oil containing only hydrogen and carbon atoms.

The preferred volatile hydrocarbon-based oils which are suitable for the composition according to the invention are, in particular, isoparaffins, i.e., branched alkanes containing from 8 to 16 carbon atoms, such as the "Isopar" and the Permethyl products, and in particular isododecane (also known as 2,2,4,4,6-pentamethylheptane). Needless to say, it is also possible to use mixtures of such isoparaffins. Other volatile hydrocarbon-based oils, such as petroleum distillates, in particular those sold under the name Shell Solt by the company Shell, can also be used.

The volatile organic solvent can be present in the composition according to the invention in a content ranging from 35% to 75% by weight relative to the total weight of the composition, preferably from 45% to 70% by weight, and better still, from 50% to 65% by weight.

Volatile organic solvents which can also be used are volatile silicones such as, for example, cyclic and volatile silicone oils, such as octamethylcyclotetrasiloxane, decamethylcyclopentasiloxane, dodecamethylcyclohexasiloxane, linear volatile silicones such as octamethyltrisiloxane, heptamethylhexyltrisiloxane and heptamethyloctyltrisiloxane, or alternatively volatile fluoro oils such as nonafluoromethoxybutane or perfluoromethylcyclopentane.

The liquid fatty phase can also contain non-volatile oils, and in particular non-volatile hydrocarbon-based and/or silicone-based and/or fluoro oils. Non-volatile hydrocarbon-based oils which may be mentioned in particular are:

hydrocarbon-based oils of animal origin, such as perhydrosqualene;

hydrocarbon-based oils of plant origin, such as liquid triglycerides of fatty acids of 4 to 10 carbon atoms, such as triglycerides of heptanoic or octanoic acids, or alternatively sunflower oil, grape seed oil, sesame oil, corn oil, apricot oil, castor oil, avocado oil, olive oil, cereal germ oil, soybean oil, sweet almond oil, palm oil, rapeseed oil, cotton oil, hazelnut oil, macadamia oil, jojoba oil, caprylic/capric acid triglycerides, such as those sold by the company Stéarineries Dubois or those sold under the names Miglyol 810, 812 and 818 by the company Dynamit Nobel, or karite butter;

linear or branched hydrocarbons of mineral or synthetic origin, such as petroleum jelly, polydecenes or hydrogenated polyisobutene such as parleam;

synthetic esters and ethers, such as the oils of formula $R_{10}COOR_{11}$ in which $R_{10}$ represents a higher fatty acid residue containing from 6 to 29 carbon atoms and $R_{11}$ represents a hydrocarbon-based chain containing from 3 to 30 carbon atoms, such as purcellin oil, isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate; polyol esters, such as propylene glycol dioctanoate, neopentyl glycol diheptanoate, diethylene glycol diisononanoate and pentaerythritol esters;

fatty alcohols which are liquid at room temperature, containing a branched and/or unsaturated carbon chain containing from 12 to 26 carbon atoms, such as octyldodecanol, isostearyl alcohol, oleyl alcohol, 2-hexyldecanol, 2-butyloctanol or 2 undecylpentadecanol;

higher fatty acids, such as myristic acid, palmitic acid, stearic acid, behenic acid, oleic acid, linoleic acid, linolenic acid or isostearic acid;

and mixtures thereof.

The non-volatile silicone oils which can be used in the composition according to the invention can be oils of low viscosity, such as linear polysiloxanes in which the degree of polymerization is preferably from 6 to 2000 approximately. Mention may be made, for example, of polydimethylsiloxanes (PDMSs) with a viscosity of greater than 10 mPa.s, phenyl dimethicones, phenyl trimethicones, polyphenylmethylsiloxanes and mixtures thereof.

The non-volatile oils can be present in the composition according to the invention in a content ranging from 0% to 5% by weight, relative to the total weight of the composition, preferably from 0% to 2% by weight, and better still from 0.1% to 2% by weight.

The liquid fatty phase can also contain waxes to ensure good covering of the eyelashes and to maintain the curling.

The wax present in the composition according to the invention can be chosen from waxes of animal origin, waxes of plant origin, waxes of mineral origin, synthetic waxes and various fractions of waxes of natural origin. The waxes can be present in a content ranging from 2% to 40% by weight relative to the total weight of the composition, preferably from 5% to 30% by weight, and better still from 10% to 25% by weight.

Advantageously, the wax can be chosen from the waxes (I) which have a melting point ranging from 70° C. to 110° C. These waxes in particular have a needle penetration ranging from 1 to 7.5. The needle penetration of the waxes is determined according to French standard NF T 60-123 or US standard ASTM D 1321, at a temperature of 25° C. According to these standards, the needle penetration is a measurement of the depth, expressed in tenths of a millimeter, to which a standardized needle weighing 2.5 g placed in a mobile assembly weighing 97.5 g and placed on the wax to be tested, for 5 seconds, penetrates into the wax.

The waxes (I) can, for example, be chosen in particular from rice bran wax, carnauba wax, ouricury wax, candelilla wax, montan waxes, sugarcane wax, and certain polyethylene waxes which correspond to the criteria of the waxes (I).

Advantageously, the composition according to the invention can comprise an amount of waxes (I) ranging from 0.1% to 20% by weight relative to the total weight of the composition, and preferably from 1% to 10% by weight.

According to one embodiment of the composition according to the invention, the composition can comprise at least one wax (Ia) with a melting point of greater than or equal to 70° C. and less than 83° C. and/or one wax (Ib) with a melting point ranging from 83° C. to 110° C.

Waxes (Ia) which may be mentioned, for example, are rice bran wax and candelilla wax. Waxes (Ib) which may be mentioned, for example, are carnauba wax, ouricury wax and montan waxes. Carnauba wax is preferably used.

Advantageously, the composition according to the invention can comprise a mixture of waxes (I) containing at least one first wax (Ia) and at least one second wax (Ib) as defined above.

The said mixture of waxes (I) can comprise from 5% to 50% by weight of wax (Ia), relative to the total weight of the said mixture of waxes (I), and from 50% to 95% by weight of wax (Ib).

The composition can also comprise at least one wax (II) known as a soft wax, which has a melting point of greater than or equal to 45° C. and less than 70° C. The wax (II) can advantageously have a needle penetration of greater than 7.5 and preferably less than or equal to 217, measured according to the conditions defined above for the waxes (I). This wax (II) makes it possible in particular to make the coating deposited on the eyelashes flexible.

These waxes (II) can be chosen in particular from beeswax, lanolin waxes, paraffin waxes, ceresin waxes, microcrystalline waxes, ozokerites, spermacetis, certain polyethylene waxes with a molecular weight such that they correspond to the criteria of the waxes (II), and hydrogenated plant oils.

Among the hydrogenated plant oils which may be mentioned are hydrogenated jojoba waxes and hydrogenated oils which are obtained by catalytic hydrogenation of fatty substances composed of a linear or non-linear $C_8$–$C_{32}$ fatty chain and which have the qualities corresponding to the definition of the waxes. Mention may be made in particular of hydrogenated sunflower oil, hydrogenated castor oil, hydrogenated cotton oil, hydrogenated coconut oil and hydrogenated lanolin.

Advantageously, the wax (I) and the wax (II) can be present in the composition according to a wax (I)/wax (II) weight ratio which can range from 0.2 to 1, and preferably ranges from 0.4 to 0.7.

The composition according to the invention can also contain an auxiliary lipophilic film-forming polymer in the liquid fatty phase. This auxiliary lipophilic film-forming polymer may in particular be soluble, or alternatively so-called liposoluble, in the liquid fatty phase. This lipophilic film-forming polymer in particular imparts good staying power to the composition after it has been applied to the keratin fibres.

Lipophilic polymers which may be mentioned in particular are copolymers resulting from the copolymerization of at least one vinyl ester and of at least one other monomer which may be an olefin, an alkyl vinyl ether or an allylic or methallylic ester, as described in French patent application FR-A-2,232,303, the content of which is incorporated into the present application by way of reference.

As lipophilic film-forming polymers which can be used in the invention, mention may also be made of polyalkylenes, and in particular $C_2$–$C_{20}$ alkene copolymers, such as polybutene, alkylcelluloses with a linear or branched, saturated or unsaturated $C_1$ to $C_8$ alkyl radical, such as ethylcellulose and propylcellulose, copolymers of vinylpyrrolidone (VP) and in particular copolymers of vinylpyrrolidone and of $C_2$ to $C_{40}$ and better still $C_3$ to $C_{20}$ alkene. As examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene and VP/acrylic acid/lauryl methacrylate copolymers.

The auxiliary lipophilic film-forming polymer in the liquid fatty phase can be present in the composition in a content ranging from 0.5% to 15% by weight relative to the total weight of the composition, and better still from 2% to 10% by weight.

The composition according to the invention can also comprise a thickener for the liquid fatty phase. The thickener can be chosen from organomodified clays which are clays treated with compounds chosen in particular from quaternary amines and tertiary amines. Organomodified clays which may be mentioned are organomodified bentonites, such as those sold under the name "Bentone 34" by the company Rheox, organomodified hectorites, such as those sold under the name "Bentone 27" and "Bentone 38" by the company Rheox. These clays are generally combined, in a known manner, with an activator such as propylene carbonate or ethanol in order to obtain thickening of the liquid fatty phase.

The thickener can be present in a content ranging from 0.5% to 10% by weight relative to the total weight of the composition, and better still from 1% to 7% by weight.

In the composition according to the invention, the total weight of the liquid fatty phase can range from 65% to 99% by weight relative to the total weight of the composition, and better still from 80% to 99% by weight.

The composition can also comprise at least one dyestuff, such as pulverulent compounds and/or liposoluble dyes, for example in a proportion of from 0.01 to 30% of the total weight of the composition. The pulverulent compounds can be chosen from pigments and/or nacres and/or fillers, other than those described above, usually used in cosmetic or dermatological compositions. Advantageously, the pulverulent compounds represent from 0.1 to 25% of the total weight of the composition, and better still from 1 to 20%.

The pigments can be white or colored, and mineral and/or organic. Mineral pigments which may be mentioned are titanium dioxide, optionally surface-treated, zirconium oxide or cerium oxide, as well as iron oxide or chromium oxide, manganese violet, ultramarine blue, chromium hydrate and ferric blue. Organic pigments which may be mentioned are carbon black, pigments of D & C type and lakes based on cochineal carmine, barium, strontium, calcium or aluminium.

The nacreous pigments can be chosen from white nacreous pigments such as mica coated with titanium or with bismuth oxychloride, colored nacreous pigments such as titanium mica with iron oxides, titanium mica with, in particular, ferric blue or chromium oxide, titanium mica with an organic pigment of the abovementioned type, and nacreous pigments based on bismuth oxychloride.

The composition according to the invention can also contain ingredients commonly used in cosmetics, such as vitamins, trace elements, softeners, sequestering agents, fragrances, dimethicone copolyols, ceramides, cohesion agents, acidifying or basifying agents usually used in cosmetics and preserving agents, or mixtures thereof.

Needless to say, a person skilled in the art will take care to select this or these optional additional compounds, and/or the amount thereof, such that the advantageous properties of the composition according to the invention are not, or are not substantially, adversely affected by the addition envisaged.

The composition according to the invention can be prepared in a manner known to a person skilled in the art by first melting the waxes and mixing the ingredients of the fatty phase, including the lipophilic additives. The pigments and fillers are then added, along with the prethickened solvents. The aqueous phase is then prepared by mixing the constituents together and the aqueous phase is dispersed in the fatty phase.

The composition according to the invention is intended for a mascara product comprising a reservoir, containing the mascara composition, and a system for applying the composition to keratin fibres, in particular the eyelashes. The reservoir is fitted, in a known manner, with an aperture in which is housed a draining system. The applicator system comprises a shaft fitted at one end with a brush and at a second end with a stopper intended to close the reservoir. Such packaging is illustrated in particular in FIG. 7 of European patent application EP-A-611,170 which is incorporated herein by way of reference.

The invention is illustrated in greater detail in the examples which follow.

Method for Measuring the Shrinkage

The measuring principle includes of measuring the length of a test piece of isolated stratum corneum before treatment and after treatment, and then determining the percentage of shrinkage of the test piece based on these measurements.

1 cm×0.4 cm test pieces of stratum corneum ranging from 10 to 20 µm in thickness are used, placed on an MTT 610 extensiometer sold by the company Diastron.

The test piece is placed between two jaws and then left for 12 hours in an atmosphere at 30° C. and 40% relative humidity.

The test piece is stretched at a speed of 2 mm/minute to a length of between 5 and 10% of the initial length in order to determine the length ($l_1$) from which the test piece begins to exert a force on the jaws which is detected by the machine.

The test piece is then relaxed and 2 mg of an aqueous 7% by weight polymer composition is applied to the stratum corneum. After total evaporation of the composition, the test piece is stretched under the same conditions as described above in order also to determine the length ($l_2$) for the treated test piece.

The percentage of shrinkage is then determined by the ratio: $100 \times (l_2 - l_1)/l_1$.

EXAMPLE 1

A mascara having the composition below was prepared:

| | |
|---|---|
| Carnauba wax | 4.6 g |
| Rice bran wax | 2.1 g |
| Paraffin | 2.2 g |
| Beeswax | 7.9 g |
| Wheat protein hydrolysate (Tritisol from the company Croda) | 0.34 g |
| Talc | 1 g |
| Bentonite | 5 g |
| Vinyl acetate/allyl stearate copolymer (65/35) | 6.5 g |
| Polyvinyl laurate (Mexomer PP from Chimex) | 0.7 g |
| Sulphopolyester (AQ 55S from Eastman Chemical) | 0.12 g |
| Isododecane | 53.9 g |
| Propylene carbonate | 1.6 g |
| D-Panthenol | 0.2 g |
| Pigments | 4.9 g |
| Preserving agents qs | |
| Water qs | 100 g |

After applying this mascara to the eyelashes, good curling of the eyelashes and a waterproof make-up effect were obtained.

EXAMPLE 2

Comparative

A mascara having the composition below, not forming part of the invention, was prepared:

| | |
|---|---|
| Carnauba wax | 4.6 g |
| Rice bran wax | 2.1 g |
| Paraffin | 2.2 g |
| Beeswax | 7.9 g |
| Wheat protein hydrolysate (tritisol from the company Croda) | 0.34 g |
| Rice starch | 0.7 g |
| Bentonite | 5 g |
| Vinyl acetate/allyl stearate copolymer (65/35) | 6.5 g |
| Polyvinyl laurate (Mexomer PP from Chimex) | 0.7 g |
| Sulphopolyester (AQ 55S from Eastman Chemical) | 0.12 g |
| Isododecane | 54.2 g |
| Propylene carbonate | 1.6 g |
| D-Panthenol | 0.2 g |
| Pigments | 4.9 g |
| Preserving agents qs | |
| Water qs | 100 g |

After applying the mascara to the eyelashes, it was found that the eyelashes were curled less than those made up with the composition of Example 1.

EXAMPLE 3

A mascara having the composition below was prepared:

| | |
|---|---|
| Carnauba wax | 4.7 g |
| Candelilla wax | 0.5 g |
| Paraffin | 2 g |
| Beeswax | 8.2 g |
| Kaolin (Kaolin Supreme 1 from English China Clays) | 1.5 g |
| Bentonite | 5.1 g |
| Vinyl acetate/allyl stearate copolymer (65/35) | 6.7 g |
| Polyvinyl laurate (Mexomer PP from Chimex) | 0.6 g |
| Isododecane | 57.2 g |
| Propylene carbonate | 1.6 g |
| Polyurethane-polyether as an aqueous dispersion containing 38% solids (Avalure UR450 from Goodrich) | 0.76 g |
| Deoxyribonucleic acid | 0.02 g |
| Pigments | 5.2 g |
| Preserving agents qs | |
| Water qs | 100 g |

After applying this mascara to the eyelashes, good curling of the eyelashes and a water-resistant make-up effect were obtained.

EXAMPLE 4

A mascara having the composition below was prepared:

| | |
|---|---|
| Jojoba wax | 1 g |
| Carnauba wax | 3.2 g |
| Rice bran wax | 3.5 g |
| Paraffin | 3 g |
| Beeswax | 7.9 g |
| Mica (Mica Concord 1000 from Sciama) | 2 g |
| Bentonite | 5 g |
| Propylene carbonate | 1.6 g |
| Vinyl acetate/allyl stearate copolymer (65/35) | 5.5 g |
| Polyvinyl laurate (Mexomer PP from Chimex) | 1 g |
| Sulphopolyester (AQ 55S from Eastman Chemical) | 0.15 g |
| Isododecane | 55.1 g |
| Pigments | 5 g |
| Preserving agents qs | |
| Water qs | 100 g |

After applying this mascara to the eyelashes, good curling of the eyelashes and a waterproof make-up effect are obtained.

What is claimed is:

1. A cosmetic composition for coating keratin fibres, said composition comprising
   (a) a liquid fatty phase containing at least one volatile organic solvent;
   (b) an aqueous phase containing a polymer system comprising at least one film-forming polymer, wherein the film-forming polymer is dispersed in the aqueous phase as solid particles, and wherein the aqueous phase is dispersed in the liquid fatty phase; and
   (c) at least one lamellar filler.

2. The composition according to claim 1, wherein the keratin fibres are eyelashes.

3. The cosmetic composition according to claim 1, wherein said polymer system is capable of forming a film, which, at a concentration of 7% in water, produces a shrinkage of isolated stratum corneum of more than 1% at 30° C. and at a relative humidity of 40%.

4. The cosmetic composition according to claim 1, wherein said film-forming polymer is an anionic polyester.

5. The cosmetic composition according to claim 4, wherein the anionic polyester comprises at least one monomer bearing a group —$SO_3M$ in which M is chosen from hydrogen, an ammonium ion, and metal ions.

6. The cosmetic composition according to claim 4, wherein the polyester is a copolymer of at least one dicarboxylic acid, of at least one diol, and of at least one difunctional aromatic monomer bearing a group —$SO_3M$ in which M is chosen from hydrogen, an ammonium ion, and metal ions.

7. The cosmetic composition according to claim 6, wherein the dicarboxylic acid is chosen from phthalic acid, isophthalic acid, and terephthalic acid.

8. The cosmetic composition according to claim 6, wherein the diol is chosen from ethylene glycol, diethylene glycol, triethylene glycol, 1,3-propanediol, 1,4-cyclohexanedimethanol, and 1,4-butanediol.

9. The cosmetic composition according to claim 6, wherein the difunctional aromatic monomer bearing the group —$SO_3M$ is chosen from sulphoisophthalic acids, sulphoterephthalic acids, sulphophthalic acids, 4-sulphonaphthalene-2,7-dicarboxylic acids, and salts thereof.

10. The cosmetic composition according to claim 9, wherein the difunctional aromatic monomer bearing the group —$SO_3M$ is the sodium salt of 5-sulphoisophthalic acid.

11. The cosmetic composition according to claim 1, wherein the film-forming polymer is chosen from anionic polyurethanes.

12. The cosmetic composition according to claim 11, wherein the anionic polyurethanes are chosen from polyether-polyurethanes and polyester-polyurethanes.

13. The cosmetic composition according to claim 1, wherein the film-forming polymer is present in an amount ranging from 0.05% to 10% by weight of active material relative to the total weight of the composition.

14. The cosmetic composition according to claim 13, wherein the film-forming polymer is present in an amount ranging from 0.1 to 7% by weight of active material relative to the total weight of the composition.

15. The cosmetic composition according to claim 1, wherein the aqueous phase further comprises at least one additional film-forming polymer, wherein said additional film-forming polymer is water-soluble.

16. The cosmetic composition according to claim 1, wherein the polymer system further comprises at least one auxiliary film-forming agent.

17. The cosmetic composition according to claim 1, wherein the volatile organic solvent is chosen from volatile hydrocarbon-based oils.

18. The cosmetic composition according to claim 17, wherein the volatile hydrocarbon-based oils are chosen from isoparaffins containing from 8 to 16 carbon atoms.

19. The cosmetic composition according to claim 1, wherein the volatile organic solvent is present in an amount ranging from 35% to 75% by weight relative to the total weight of the composition.

20. The cosmetic composition according to claim 19, wherein the volatile organic solvent is present in an amount ranging from 45% to 70% by weight relative to the total weight of the composition.

21. The cosmetic composition according to claim 20, wherein the volatile organic solvent is present in an amount ranging from 50% to 65% by weight relative to the total weight of the composition.

22. The cosmetic composition according to claim 1, wherein the liquid fatty phase further comprises at least one auxiliary lipophilic film-forming polymer.

23. The cosmetic composition according to claim 1, wherein the liquid fatty phase further comprises at least one wax.

24. The cosmetic composition according to claim 23, wherein the at least one wax is present in an amount ranging from 2% to 40% by weight relative to the total weight of the composition.

25. The cosmetic composition according to claim 24, wherein the at least one wax is present in an amount ranging from 5% to 30% by weight relative to the total weight of the composition.

26. The cosmetic composition according to claim 25, wherein the at least one wax is present in an amount ranging from 10% to 25% by weight relative to the total weight of the composition.

27. The cosmetic composition according to claim 23, wherein the at least one wax has a melting point ranging from 70° C. to 110° C. (wax I).

28. The cosmetic composition according to claim 27, wherein the at least one wax (I) is present in an amount ranging from 0.1% to 20% by weight relative to the total weight of the composition.

29. The cosmetic composition according to claim 23, further comprising at least one additional wax, wherein said at least one additional wax has a melting point of greater than or equal to 45° C. and less than 70° C. (wax II).

30. The cosmetic composition according to claim 29, wherein the wax (II) is present in a wax (I)/wax (II) weight ratio ranging from 0.2 to 1.

31. The cosmetic composition according to claim 1, wherein the liquid fatty phase is present in an amount ranging from 65% to 99% by weight relative to the total weight of the composition.

32. The cosmetic composition according to claim 1, wherein the aqueous phase is present in an amount ranging from 1% to 35% by weight relative to the total weight of the composition.

33. The cosmetic composition according to claim 1, wherein the lamellar filler is chosen from talc, mica, boron nitride, kaolin, silica, and mixtures thereof.

34. The cosmetic composition according to claim 1, wherein the lamellar filler is present in an amount ranging from 0.5% to 10% by weight relative to the total weight of the composition.

35. The cosmetic composition according to claim 1, wherein the lamellar filler is present in an amount ranging from 0.5% to 5% by weight relative to the total weight of the composition.

36. The cosmetic composition according to claim 1, wherein the liquid fatty phase further comprises at least one thickener.

37. The cosmetic composition according to claim 1, further comprising at least one additive chosen from vitamins, trace elements, softeners, sequestering agents, fragrances, dimethicone copolyols, ceramides, cohesion agents, preserving agents, and mixtures thereof.

38. The cosmetic composition according to claim 1, wherein the composition is a make-up composition for coating keratin fibres, a make-up base for coating keratin fibres, a composition for coating keratin fibres that is applied over a make-up, or a composition for cosmetically treating keratin fibres.

39. A mascara product comprising
   (a) a reservoir containing a mascara composition, wherein the mascara composition comprises
      (1) a liquid fatty phase containing at least one volatile organic solvent;
      (2) an aqueous phase containing a polymer system comprising at least one film-forming polymer, wherein the film-forming polymer is dispersed in the aqueous phase as solid particles, and wherein the aqueous phase is dispersed in the liquid fatty phase; and
      (3) at least one lamellar filler; and
   (b) a system for applying said composition to keratin fibres.

40. A process for coating keratin fibres, said process comprising applying to said keratin fibres a composition comprising
   (a) a liquid fatty phase containing at least one volatile organic solvent;
   (b) an aqueous phase containing a polymer system comprising at least one film-forming polymer, wherein the film-forming polymer is dispersed in the aqueous phase as solid particles, and wherein the aqueous phase is dispersed in the liquid fatty phase; and
   (c) at least one lamellar filler.

41. The process according to claim 40, wherein the keratin fibres are eyelashes.

42. A process of coating keratin fibres to curl said fibres and/or to provide waterproofing to said fibres and/or to lengthen said fibres, said process comprising applying to said keratin fibres a composition comprising
   (a) a liquid fatty phase containing at least one volatile organic solvent;
   (b) an aqueous phase containing a polymer system comprising at least one film-forming polymer, wherein the film-forming polymer is dispersed in the aqueous phase as solid particles, and wherein the aqueous phase is dispersed in the liquid fatty phase; and
   (c) at least one lamellar filler.

43. The process according to claim 42, wherein the keratin fibres are eyelashes.

* * * * *